United States Patent [19]

Cammarata

[11] 4,295,270
[45] Oct. 20, 1981

[54] ELECTRODE POSITIONING SYSTEM
[75] Inventor: Jacob J. Cammarata, Crystal, Minn.
[73] Assignee: Medtronic, Inc., Minneapolis, Minn.
[21] Appl. No.: 84,802
[22] Filed: Oct. 15, 1979
[51] Int. Cl.³ .............................................. H01B 13/20
[52] U.S. Cl. ........................................ 29/828; 29/867
[58] Field of Search ................ 29/825, 828, 857, 867, 29/868, 869; 174/75 C

[56] References Cited
U.S. PATENT DOCUMENTS
3,621,560 11/1971 LeBright .............................. 29/828
4,059,330 11/1977 Shirey ................................... 29/828

FOREIGN PATENT DOCUMENTS
2156294 5/1973 Fed. Rep. of Germany ........ 29/828

Primary Examiner—Nicholas P. Godici
Assistant Examiner—C. J. Arbes
Attorney, Agent, or Firm—Schroeder, Siegfried, Ryan, Vidas, Steffey & Arrett

[57] ABSTRACT

A system for positioning a ring electrode at a desired location on, and in electrical communication with, the outer, braided conductor of a coaxial body implantable electrical stimulation lead. The outer insulation is stripped from the desired electrode location to one end of the lead to expose the braided conductor. The exposed braided conductor is pushed back from the one lead end to expose that end and at least a portion of the exposed lead end is severed. The braided conductor is then repositioned so as to extend past the previously exposed lead end with the extending portion of the braided conductor being wrapped about itself to form a twist. The twist preferably comes to a point but, in any event, has a diameter smaller than the remainder of the braided conductor so as to be easily threaded through a ring electrode having an inside diameter generally identical to the outside diameter of the braided conductor. The braided conductor is threaded through the ring electrode until the ring electrode is in the desired electrode position. The exposed braided conductor that does not underlie the ring electrode may be removed and the lead may be provided with a tip electrode in electrical communication with the innermost conductor, in known manner. Insulation provided to the region between the ring and tip electrode will maintain the ring electrode in the desired position. In a preferred embodiment, the ring electrode may be provided with a portion of smaller outside diameter than the electrode-forming surface. This smaller diameter portion may be crimped to assure the integrity of the electrical communication between the ring electrode and braided conductor as well as to help maintain the ring electrode in the desired location. Insulation applied over this smaller diameter ring electrode portion will provide a lead of uniform cross-section throughout, as well as cover any irregularities resulting from the crimping operation to eliminate areas of high current density that might otherwise result from such surface irregularities.

6 Claims, 11 Drawing Figures

ELECTRODE POSITIONING SYSTEM

DESCRIPTION

BACKGROUND OF PRIOR ART

The use of electrically conductive leads for the delivery of body stimulation energy is known to the prior art. Typically such leads employ one or more conductors insulated from the body environment, and themselves, by an insulating material with the conductors being in electrical communication with electrodes carried by the lead body. In the context of temporary cardiac pacing, it has become common practice to employ coaxial leads of a type having a multifilament inner conductor and a braided outer conductor separated by a sheath of insulation with the outer braided conductor also being insulated.

Typical coaxial leads of the type discussed above are provided with an electrode pair adjacent the distal end thereof, usually in the form of a ring electrode in electrical communication with the braided conductor and a tip electrode in electrical communication with the inner conductor. The positioning of the tip electrode and the establishment of electrical communication between it and the inner conductor is relatively straightforward. However, the prior art systems by which the ring electrode is positioned, and the electrical communication between it and the braided conductor is established, are cumbersome and not totally reliable.

In all known ring electrode placement systems, the first step is to strip the outermost insulation from the desired ring electrode location to that end of the lead at which the tip electrode will be positioned. In one system, following the stripping step, a ring having a larger inner diameter than the outer diameter of the braided conductor is then positioned at the desired ring electrode location. The excess braided conductor which extends between the positioned ring electrode and the lead end is then jammed under the ring electrode to establish a mechanical and electrical engagement between the braided conductor and the ring electrode. While this system allows the ring electrode to be positioned in the desired location with relative ease, the jamming of the braided conductor under the ring is potentially damaging to the braided conductor material and its effectiveness in establishing the mechanical and electrical connection cannot be viewed, inasmuch as the connection is obscured by the ring electrode itself.

Another system by which a ring electrode is positioned, and an electrical communication between it and the outer braided conductor is established, employs a ring underlying the braided conductor at the desired electrode location. This ring increases the braided conductor diameter at the desired electrode location. The desired electrode location is then coated with a silver epoxy and the ring electrode is threaded over the lead. The ring electrode has a diameter approximately equal to that of the braided conductor at the desired electrode location such that a force fit is established to maintain the electrode in position. The silver epoxy, being conductive, facilitates the electrical communication between the braided conductor and the ring electrode. While this system has proven commercially feasible, it nonetheless requires excessive manipulation. In addition, the use of silver epoxy requires a high degree of care so that it is contained within the desired electrode location.

BRIEF SUMMARY OF THE INVENTION

The present invention provides a system for positioning a ring electrode at a desired location on, and in electrical communication with, the outer, braided conductor of a coaxial body implantable electrical stimulation lead. This system requires less manipulation than the last of the above-described prior art systems while providing a more reliable mechanical and electrical contact between the ring electrode and the braided conductor than the first of the above-described prior art systems. After the outer insulation is stripped from the desired electrode location to the distal end of the lead, the exposed braided conductor is pushed back from that end to expose the insulation between the inner and outer conductors. At least a portion of the exposed inner insulation, and the conductor it contains, is severed with the braided conductor then being repositioned to extend past the end of the inner insulation and conductor. The extending portion of the braided conductor is then wound about itself so as to form a twist, the twist having a smaller diameter than the braided conductor and preferably coming to a point. The twist may be easily inserted into a ring electrode having an inside diameter generally identical to the outside diameter of the braided conductor. Thus, the twist facilitates the threading of the ring by the braided conductor such that the ring may be moved along the braided conductor to the desired electrode location. The braided conductor extending between the ring electrode and the distal end of the lead may then be removed with insulation applied over that region to maintain the ring electrode in position. In a preferred embodiment, the ring electrode is provided with a portion of smaller diameter than the electrode-forming portion, the smaller diameter portion being crimped down on the braided conductor to enhance the electrical and mechanical communication therewith. The smaller diameter portion of the ring electrode may be covered with insulation so as to eliminate areas of high current density resulting from surface irregularities from the crimping operation. A tip electrode may be provided at the distal end of the lead to form an electrode pair with the ring electrode, the tip electrode being in mechanical and electrical communication with the inner conductor, in known manner.

DETAILED DESCRIPTION OF THE INVENTION

Figure 1:
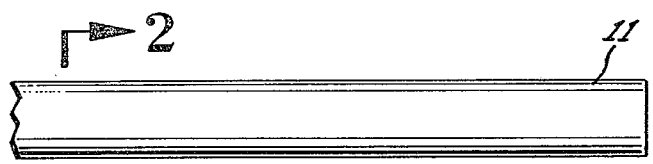
FIG. 1 illustrates a prior art coaxial lead body employed within the system of the present invention.
Figure 2:
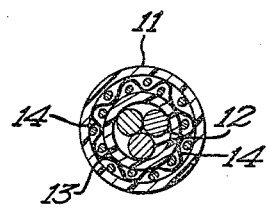
FIG. 2 illustrates a cross-section of the lead body of FIG. 1 taken along the line 2—2 in FIG. 1.

FIG. 1 and FIG. 2, which is a cross-section taken along the line 2—2 in FIG. 1, illustrate a coaxial lead body of a type employed in the prior art, in side view and cross-section, respectively. An inner conductor is formed of multiple filaments 12 (3 illustrated) which are typically wound about each other. An inner insulation sheath 13 surrounds the filaments 12 and may be formed by extruding it in place over the filaments 12. An outer conductor is formed by braiding filaments 14 around the insulating sheath 13, in known manner. The outer insulating sheath 11 surrounds the braided conductor formed by the filaments 14.

Figure 3:
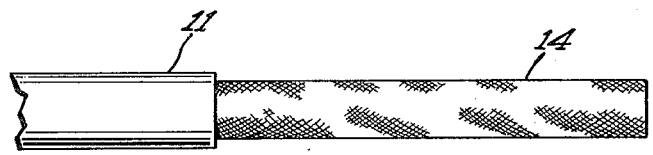
FIGS. 3–11 illustrate the various steps employed within the system of the present invention.
Figure 8:
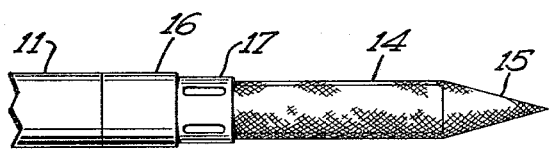
Figure 4:
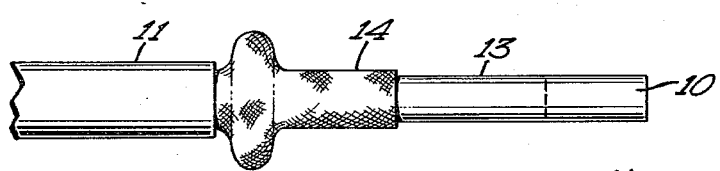
Figure 9:
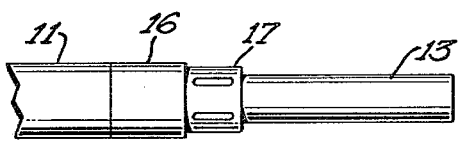
Figure 5:
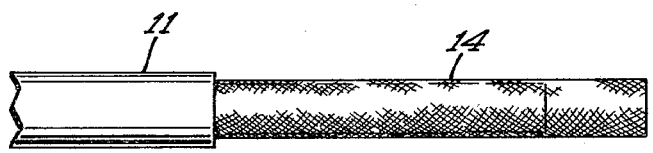
Figure 10:
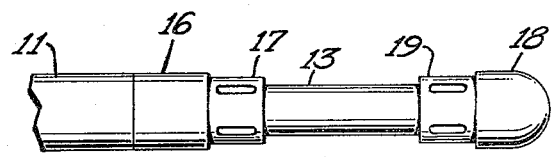
Figure 6:
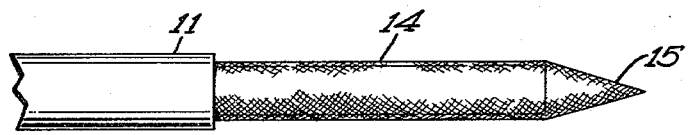
Figure 11:
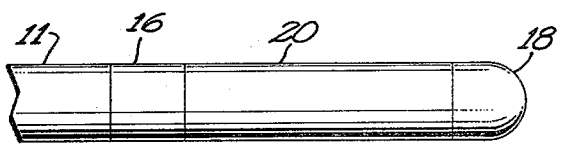
Figure 7:
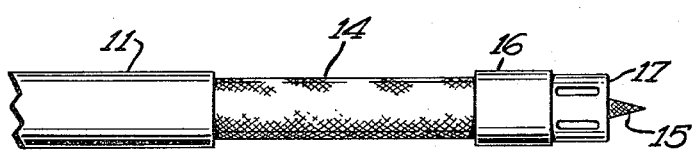

FIGS. 3-11 illustrate the various steps performed in the positioning and establishment of an electrical and mechanical contact between the braided conductor formed by filaments 14 (hereinafter referred to as braided conductor 14) and a ring electrode. In FIG. 3, the outer insulating sheath 11 is stripped from the desired electrode location to the distal end of the lead body, the end of the insulating sheath 11 defining one side of the desired electrode location. The braided conductor 14 is then pushed back from the distal end of the lead to expose the inner sheath 13 (See FIG. 4). The end 10 of inner sheath, together with the conductors it contains, is severed as at the dotted line (See FIG. 4). The braided conductor 14 is repositioned such that a portion of it extends past the end of inner sheath 13 (See FIG. 5). The extending portion of the braided conductor 14 is then wound around itself to form a twist 15 (See FIG. 6) preferably coming to a point. In any event, the twist 15 is of a smaller diameter than that portion of the braided conductor 14 that overlies the inner sheath 13. Thus, a ring electrode 16 having an inner inside diameter essentially identical to the outside diameter of braided conductor 14 may be easily threaded by twist 15 as illustrated in FIG. 7. Ring electrode 16 is then threaded along the exposed braided conductor 14 until it abuts against the end of the outer sheath 11 (See FIG. 8). In the position illustrated in FIG. 8, ring electrode 16 is in the desired electrode location. In a preferred embodiment, electrode 16 may be provided with a portion 17 having a diameter smaller than the electrode-forming portion of electrode 16. Electrode portion 17 may be crimped down on braided conductor 14 as illustrated in FIGS. 8-10. This crimping will enhance the mechanical contact between the ring electrode and the braided conductor 14 but, principally, will assure the integrity of the electrical communication between the electrode and conductor. The crimping may be performed on two opposing sides of electrode portion 17, around the totality of the surface or on two pairs of opposing sides. It has been found that a total crimping deformation across the diameter of electrode portion 17 of no more than 0.008 of an inch provides adequate mechanical and electrical contact between electrode and braided conductor 14 without harm to the inner sheath 13 or inner conductor filaments 12. However, the crimping may not be necessary for either mechanical or electrical considerations but does insure the integrity of those contacts.

After the electrode 16 is in position and electrode portion 17 is crimped, if desired, that portion of braided conductor 14 that does not underlie ring electrode 16 is removed (See FIG. 9). Inner sheath 13 may then be stripped to expose the filaments 12 forming the inner conductor and the tip electrode 18 positioned thereon as illustrated in FIG. 10. FIG. 10 illustrates an extending portion 19 on tip electrode 18 similar to the extending portion 17 on ring electrode 16. Any other construction may also be employed to electrically and mechanically secure tip electrode 18 to the filaments 12 forming the inner conductor. The crimping action will produce surface irregularities on the extending portions 17 and 19 (See FIGS. 8-10) which would result in high current densities at those irregularities. Therefore, the region between the ring electrode 16 and tip electrode 18 is insulated to cover the electrode portions 17 and 19. This also provides a lead of uniform cross-section throughout. Insulation may be applied by injection molding in known manner and the same as illustrated at 20 in FIG. 11.

Obviously, many modifications and variations of the present invention are possible in light of the above teachings. For example, various materials and construction techniques, known to the prior art, may be employed to fabricate the basic lead body illustrated in FIGS. 1 and 2. Also, as noted, extending electrode portion 17 of ring electrode 16 may not need to be crimped to provide adequate electrical and mechanical contact. In that event, electrode portion 17 may be eliminated. It is therefore to be understood that, within the scope of the appended claims, the present invention may be practiced otherwise than as specifically described.

I claim:

1. A method of positioning a ring electrode at a desired location on, and in electrical communication with, the outer braided conductor of a coaxial electrical lead comprising the steps of:
   stripping the outer insulation from the desired electrode location to one end of said lead to expose said braided conductor;
   pushing the exposed braided conductor back from said one lead to expose said one lead end;
   severing at least a portion of said exposed lead end;
   extending said braided conductor past said exposed lead end;
   forming the extending braided conductor into a twist; and
   threading said twist and exposed braided conductor through a ring electrode having an inside diameter generally identical to the outside diameter of said braided conductor until said ring electrode overlies said desired location.

2. The method of claim 1 wherein said ring electrode has a first electrode-forming portion and a second portion of smaller diameter than said first portion and further comprising the step of crimping said second ring electrode portion.

3. The method of claim 1 further comprising the step of removing said exposed braided conductor that does not overlie said desired location.

4. The method of claim 3 further comprising the step of securing a tip electrode at said exposed lead end.

5. The method of claim 4 further comprising the step of applying insulation to said lead in the region between said ring and tip electrodes.

6. The method of claim 5 wherein said ring electrode has a first electrode-forming portion and a second portion of smaller diameter than said first portion and further comprising the step of crimping said second ring electrode portion.

* * * * *